United States Patent [19]

Negishi

[11] Patent Number: 5,201,319
[45] Date of Patent: Apr. 13, 1993

[54] APPARATUS FOR MEASURING BLOOD PRESSURE

[75] Inventor: Kazuaki Negishi, Tokyo, Japan

[73] Assignee: Fukuda Denshi Co., Ltd., Tokyo, Japan

[21] Appl. No.: 903,733

[22] Filed: Jun. 24, 1992

Related U.S. Application Data

[62] Division of Ser. No. 713,248, May 29, 1991.

[30] Foreign Application Priority Data

Feb. 13, 1991 [JP] Japan .................................. 1-42567

[51] Int. Cl.⁵ .............................................. A61B 5/00
[52] U.S. Cl. .................................. 128/672; 128/677; 128/686
[58] Field of Search ........ 128/668, 672, 677, 680–684, 128/686; 606/201–203

[56] References Cited

U.S. PATENT DOCUMENTS 4,233,980 11/1980 McRae et al. ...................... 606/201

Primary Examiner—Lee S. Cohen
Assistant Examiner—Robert L. Nasser, Jr.
Attorney, Agent, or Firm—Sughrue, Mion, Zinn, Macpeak & Seas; Sughrue, Mion, Zinn et al.

[57] ABSTRACT

An apparatus for measuring blood pressure having a pole and a receiver is disclosed. The pole is fixed perpendicular to a floor. The receiver supports a subject's arm on which a cuff is wrapped around. The cuff is connected to a sphygmomanometer. Moreover, the receiver slides up and down along the pole as the body of the subject moves up and down.

3 Claims, 6 Drawing Sheets

APPARATUS FOR MEASURING BLOOD PRESSURE

This is a divisional of Application No. 07/713,248 filed May 29, 1991.

BACKGROUND OF THE INVENTION

1. Field of the Invention

The present invention relates to a method of measuring blood pressure and an apparatus for carring out the method.

More particularly, the invention relates to a method and an apparatus of measuring blood pressure of a subject changing from a squatting state to a standing state.

2. Description of the Related Art

Generally, blood pressure is pressure which blood applies to an artery system receiving blood which has been output owing to contraction of the left ventricle of the heart.

In the other words, blood pressure is pressure within a blood vessel, that is to say, internal pressure.

In detail, blood pressure includes three internal pressures: artery, vein and capillary.

However, it is usual that blood pressure is the internal pressure of artery, that is to say, arterial pressure.

The above blood pressure is defined by many factors consisting of contraction or blood volume of the heart, extension or inside diameter of the arterial wall, partial structure and adhesion of blood etc.

That is to say, blood pressure changes according to the variation of the heart, blood vessel and circulating blood volume etc.

Hence, by measuring blood pressure it is possible to discover a heart disease, determine a procedure to treat the disease, and judge the effect of the procedure.

Methods for measuring the above blood pressure are divided broadly into a direct method and an indirect method.

The direct method is a method in which blood pressure is measured directly with a transducer connected with a catheter inserted into the blood vessel.

On the contrary, the indirect method is a method in which blood pressure is measured indirectly with a cuff wrapped around an arm of a subject.

The indirect method has advantages that blood pressure is capable of being measured easily in a home owing to simple construction of an apparatus, and that it is to be measured repeatedly during a short time without pain.

Recently, in particular, the use of an automatic sphygmomanometer is now widespread among homes, which sphygmomanometer detects a Kolotkoff sound with a microphone incorporated in the cuff wrapped on the arm, and displays in digital form the maximum and minimum valves of the blood pressure measured.

Therefore, even if people have no expert knowledge, they can easily measure blood pressure with the automatic sphygmomanometer, that is to say, with the indirect method.

The prior indirect method is as follows.

That is to say, above-mentioned, blood pressure always changes, and so it is often influenced by a posture of a subject whose blood pressure is measured.

Accordingly, when blood pressure is measured, it is necessary to keep the subject in a stable environment in both mind and body.

Hence, using the prior art indirect method, first, a subject should lie on the bed or sit down on a chair.

Additionally, the subject should weaken the force in the front portion from his elbow, and stretch his arm while opening fingers of his hand, assuming a comfortable posture.

In the above-mentioned state, after a cuff is wrapped around his arm, the artery of his arm is pressed by inputting air into the cuff, thereby blood pressure is measured based on the above indirect method.

However, the conventional indirect method has the problem that it is impossible to discover high or low blood pressure which a subject has in case of standing up, that is to say, standing high blood pressure or standing low blood pressure.

The standing high or low blood pressure has been noticed recently.

For example, a splitting headache occurring the moment that a subject stands up is caused by the standing high blood pressure, thereby blood pressure rises up to 160 or more, and also the heart beat increases.

Moreover, orthostatic syncope is caused by the standing low blood pressure.

As above-mentioned, with the conventional indirect method, since blood pressure is measured by means that a subject lies on the bed or sits down on the chair, the standing high or low blood pressure cannot be determined easily.

Accordingly, a subject who has abnormality in his body as indicated by the standing high or low blood pressure, which pressure cannot be determined with the conventional indirect method, will not receive exact diagnosis and treatment.

SUMMARY OF THE INVENTION

An object of the present invention is to discover easily the standing high or low blood pressure by means of measuring a subject's blood pressure when he stands up.

The above-mentioned object can be achieved by a method of measuring blood pressure comprising, making a subject P squat down, making the body of said subject P remain in a stationary state during a fixed time in a squatting state, making said subject P stand up from said squatting state, and measuring blood pressure of said subject P in the standing state. The method of measuring blood pressure comprises the steps of: making a subject P squat down, making the body of said subject P remain in a stationary state during a fixed time in a squatting state and measuring blood pressure of said subject P, making said subject P stand up from said squatting state, measuring blood pressure of said subject P in a standing state, and comparing said blood pressure measured in said squatting state with said blood pressure measured in said standing state. An apparatus for measuring blood pressure comprises a pole 1 for being fixed perpendiculer to a floor 11, and a receiver 2 for supporting a subject P's arm on which a cuff 3 is wrapped around, said cuff 3 connected with a sphygmomanometer 4, and for sliding up and down along said pole 1 as the body of said subject P moves up and down.

BRIEF DESCRIPTION OF THE DRAWINGS

Further features and advantages of the present invention will be apparent from the detailed description below with reference to the accompanying drawings, wherein.

DESCRIPTION OF THE PREFERRED EMBODIMENTS

Figure 1:
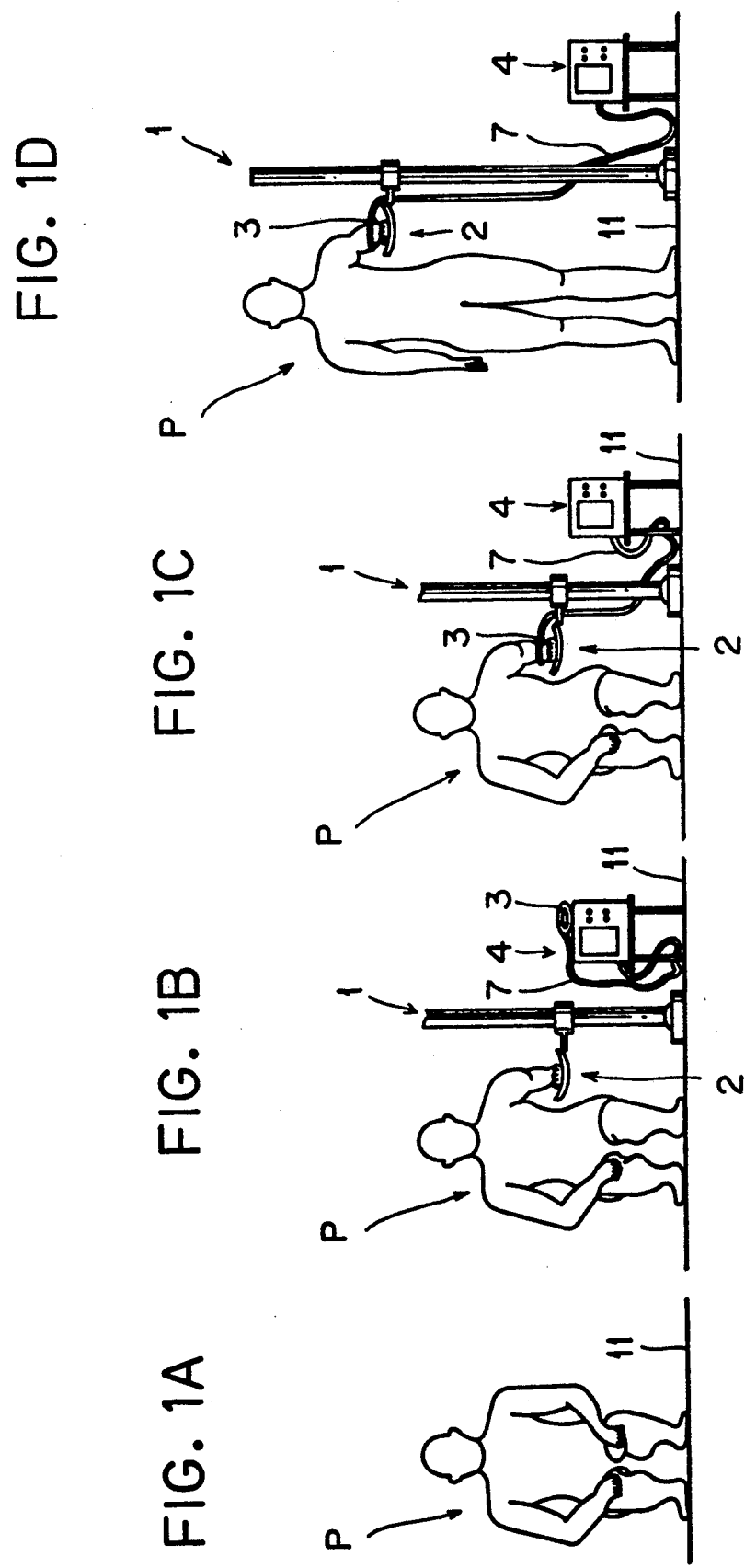
FIGS. 1A to 1D are drawings of a method in accordance with the first and second embodiments of the present invention.

FIG. 1 is a drawing of a method in accordance with the first invention of the present embodiment.

① First, a subject P squats down.

As shown in FIG. 1A, a subject P squats down on a floor 11, by bending his knees.

② Additionally, a cuff is wrapped around an arm of the subject P.

As shown in FIG. 1B, a cuff 3, which is connected with a sphygmomanometer 4 through a tube 7, is wrapped around a left arm of the subject P.

The cuff 3 together with the subject P's arm is put on a receiver 2, which receiver 2 may slide up and down along a pole 1, which pole 1 is fixed perpendiculer to the floor 11.

③ The body of the subject is maintained in a stationary state during a fixed period.

As shown in FIG. 1C, while the cuff 3 is wrapped around the arm of the subject P, as P is squatting down, his body is made to become stationary during a fixed period, for example, about 10 minutes.

④ Finally, the subject stands up, and his blood pressure is measured with the sphygmomanometer 4 at this standing state.

As shown in FIG. 1D, when the subject P stands up from his squating state (see FIG. 1C), the receiver 2, on which his arm is supported, also rises up along the pole 1, according to rising motion of his body.

When the motion of the subject P's body stops as he stands up, the rising motion of the receiver 2 also stops, and at this moment blood pressure is measured with the sphygmomanometer 4.

The indirect method with the sphygmomanometer 4, in which change of blood flow is used, is as follows.

That is to say, as well known, air is input into a bag housed within the cuff 3 through the tube 7, thereby the arm of the subject P is pressed, according to the degree of which pressure, blood flow changes.

FIG. 1 is also a drawing of a method in accordance with the second invention of the present embodiment.

① First, a subject P squats down.

As shown in FIG. 1A, a subject P squats down on a floor 11, by bending his knees.

② Additionally, a cuff is wrapped around an arm of the subject P.

As shown in FIG. 1B, a cuff 3, which is connected with a sphygmomanometer 4 through a tube 7, is wound round a left arm of the subject P.

The cuff 3 together with the subject P's arm is put on a receiver 2, which receiver 2 may slide up and down along a pole 1, which pole 1 is fixed perpendiculer to the floor 11.

③ The body of the subject is put under a stationary state during a fixed period, and his blood pressure is measured.

As shown in FIG. 1C, while the cuff 3 is wrapped around the arm of the subject P, as P is squatting down, his body is stationary during a fixed period, for example, about 10 minutes.

In this stationary state, his blood pressure is measured with the sphygmomanometer 4.

The indirect method with the sphygmomanometer 4, in which change of blood flow is used, is as follows.

That is to say, as well known, air is input into a bag housed within the cuff 3 through the tube 7, thereby the arm of the subject P is pressed, according to the degree of which pressure, blood flow changes.

④ The subject stands up, and his blood pressure is measured with the sphygmomanometer 4 at this standing state.

As shown in FIG. 1D, when the subject P stands up from his squating state (see FIG. 1C), the receiver 2, on which his arm is supported, also rises up along the pole 1, according to the motion of his body.

When the motion of the subject P's body stops as he stands up, the rising motion of the receiver 2 also stops, and at this moment blood pressure is measured with the sphygmomanometer 4.

⑤ Finally, a comparison is made of the blood pressure measured in the squatting state with the blood pressure measured in the standing state.

That is to say, since the blood pressure measured in the squatting state and the blood pressure measured in the standing state are displayed in digital form on the sphygmomanometer 4, dynamic variations of blood pressure measured by comparing them.

Figure 2:
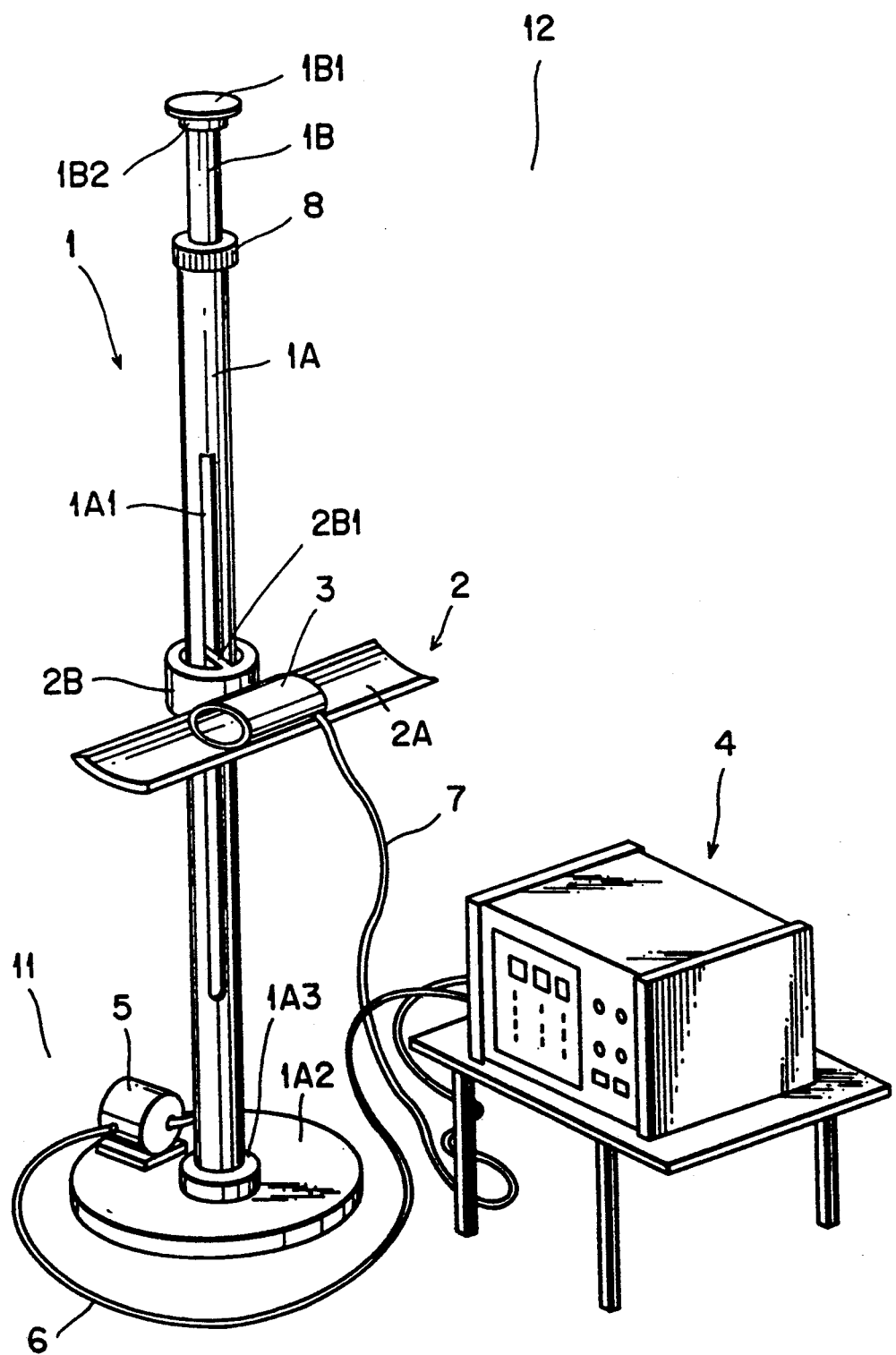
FIG. 2 is a drawing of an apparatus in accordance with a third embodiment of the present invention.

FIG. 2 is a drawing of an apparatus in accordance with the third embodiment of the present invention, in which reference numeral 1 is a pole, 2 a receiver, 3 a cuff, and 4 a sphgymomanometer.

The pole 1 is fixed perpendicular to a floor 11, which pole 1 is composed of a first tube 1A and a second tube 1B formed respectively in cylindrical shape.

The first and second tubes 1A and 1B are telescopic tubes concentric with each other.

On the top of the first tube 1A, a fastening member 8 is mounted, which fastening member 8 fastens and fixes the second tube 1B so as to apply to a ceiling 12.

Figure 6:
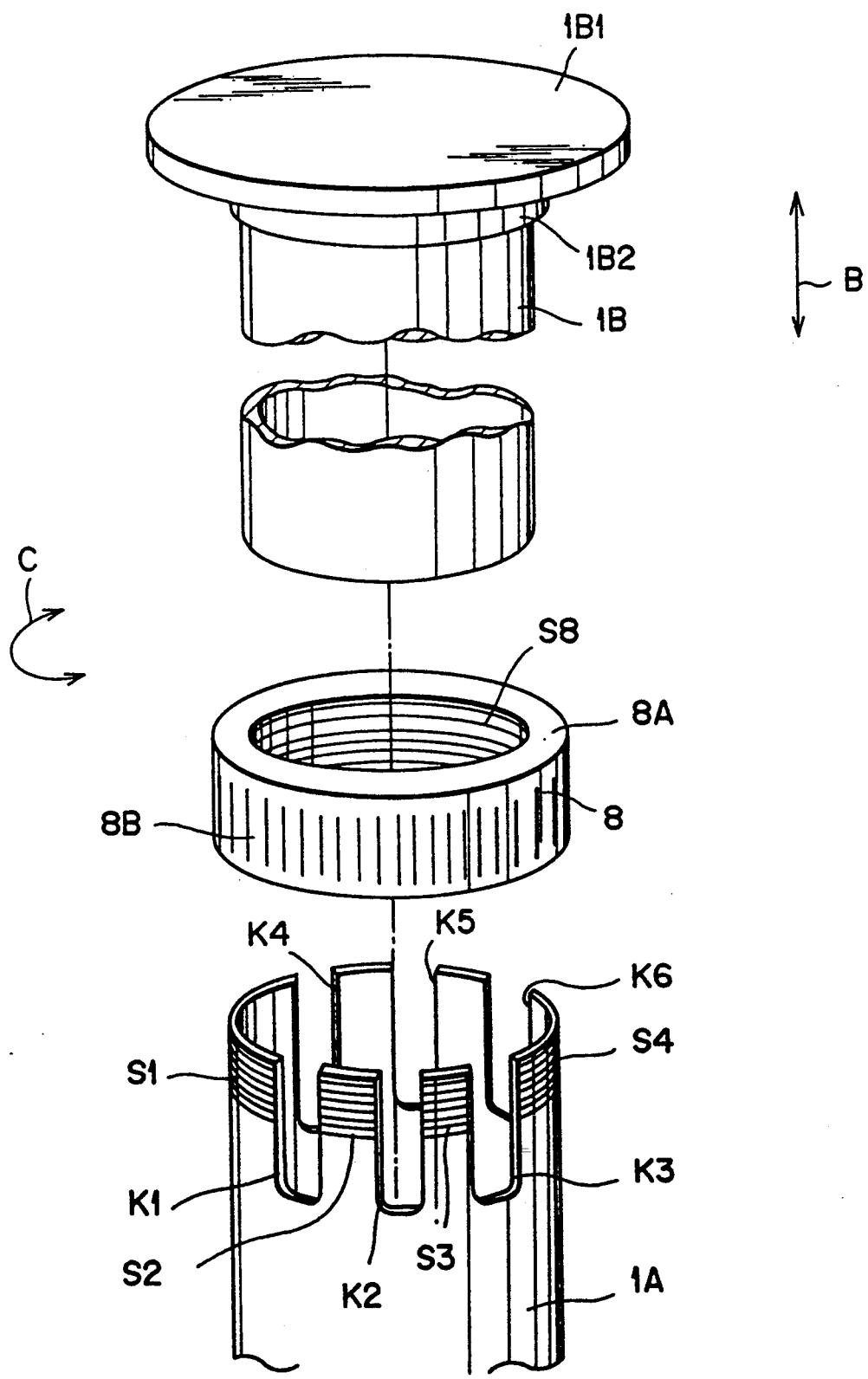
FIG. 6 is a drawing of a mechanism for adjusting the length of a pole constituting the third embodiment of the present invention.

As shown in FIG. 6, the fastening member 8 is formed in flat and cylindrical shape, an upper portion 8A of which fastening member 8 is mounted on the top of the first tube 1A, and through which fastening member 8 the second tube 1B goes so as to be inserted within the first tube 1A. Within fastening member 8, a female screw S8 is adapted to engage with male screws S1, S2 ... between notches K1, K2 ....

Thereby, when the fastening member 8 is made to rotate right and left each by putting fingers on an uneveness 8B as shown with an arrow C, the portions of the male screws S1, S2 ... respectively fasten and loosen the second tube 1B.

Accordingly, since it is possible to displace the second tube 1B up and down along the first tube 1A, the second tube 1B is capable of pushing the ceiling 12 by adjusting the height of a circular disk 1B1 fixed to the top of the second tube 1B with a supplementary member 1B2.

However, the pole 1 is not restricted to the above construction, which pole 1 may be constituted by only the first tube 1A, if it is used in a stable place.

On the bottom of the first tube 1A, a bottom plate 1A2 is disposed through a supplementary member 1A3, which supplementary member 1A3 supports the first tube 1A perpendicular to the floor 11.

With this bottom plate 1A2 and the member 1A3, the pole 1 is fixed perpendicular to the floor 11.

The receiver 2 supports the subject P's arm on which the cuff 3 is wound.

Moreover, the receiver 2 slides up and down along the pole 1 as the body of the subject P moves up and down.

The receiver 2 is constituted by a supporting plate 2A for supporting the subject P's art on which the cuff 3 is wound and a slider 2B fixed to the supporting plate 2A, as shown in FIG. 2.

Figure 3:
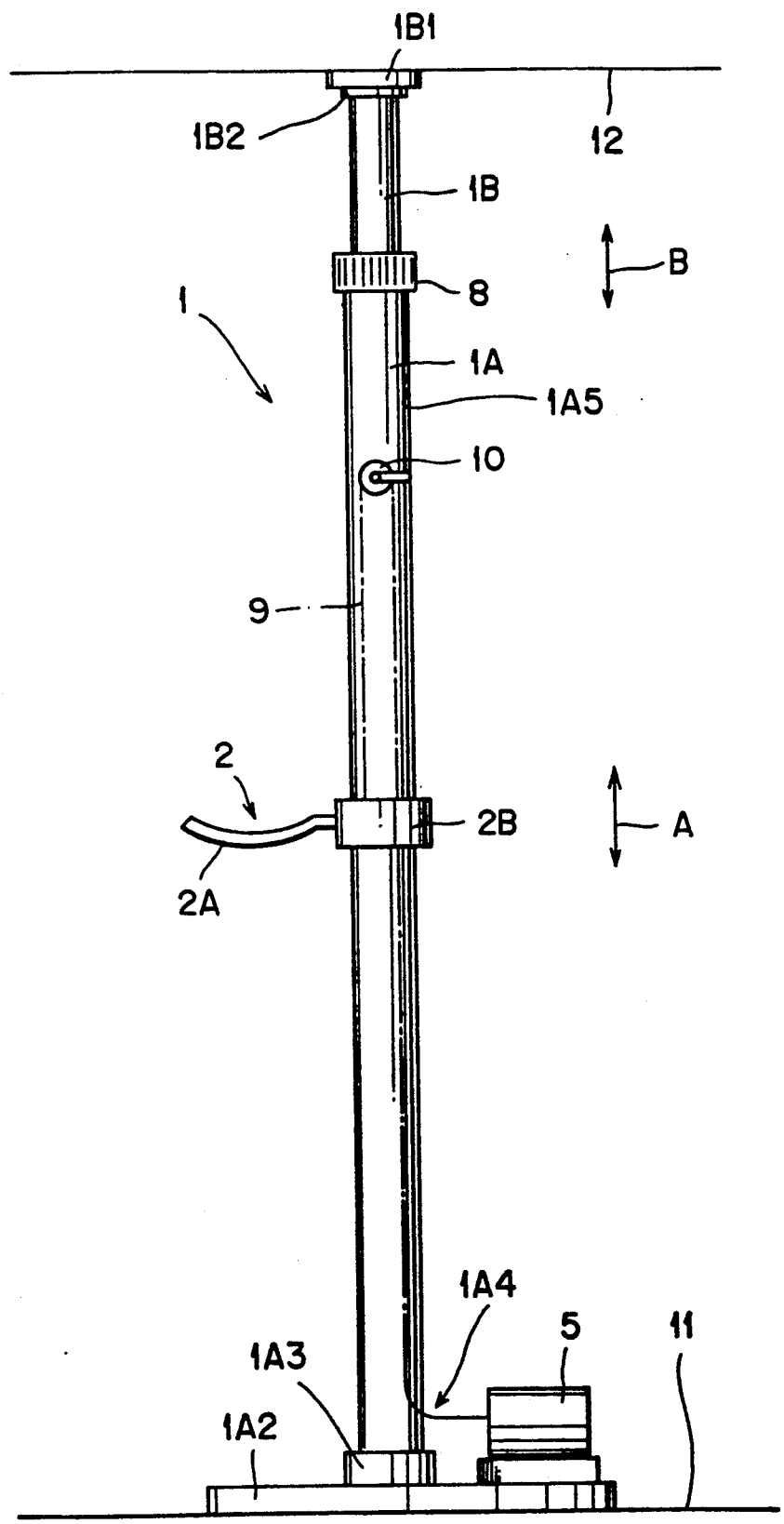
FIG. 3 is a drawing of a pole and a receiver constituting the third embodiment of the present invention.

The cross section of the supporting plate 2A is concave slightly to support easily the subject P's arm, as shown in FIG. 3.

Figure 4:
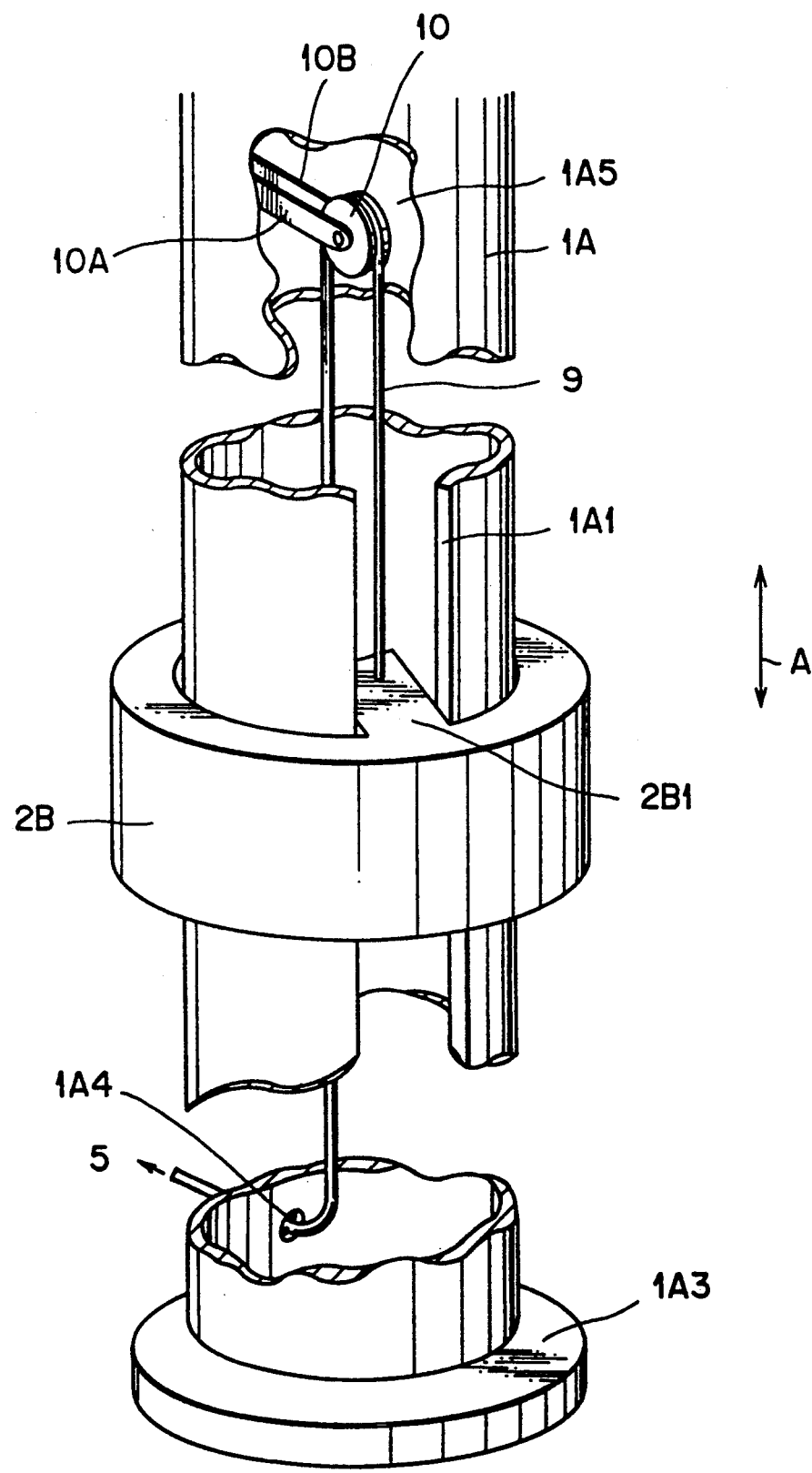
FIG. 4 is a detailed drawing of a receiver constituting the third embodiment of the present invention.

The slider 2B is formed in a cylinder shape as shown in FIGS. 2, 3 and 4, on which slider 2B a projection 2B1 elongates radially to the inside, which projection is inserted in a groove 1A1 formed axially on the first tube 1A.

That is to say, the slider 2B is to slide up and down along the groove 1A1 of the first tube 1, as shown with an arrow A.

A wire 9 is fixed to the projection 2B1 of the slider 2B, which wire 9 is capable of being wound and unwound with a motor 5 so as to slide the slider 2B along the tube 1.

As another means for sliding the slider 2B, the wire 9 may be operated by hand.

Figure 5:
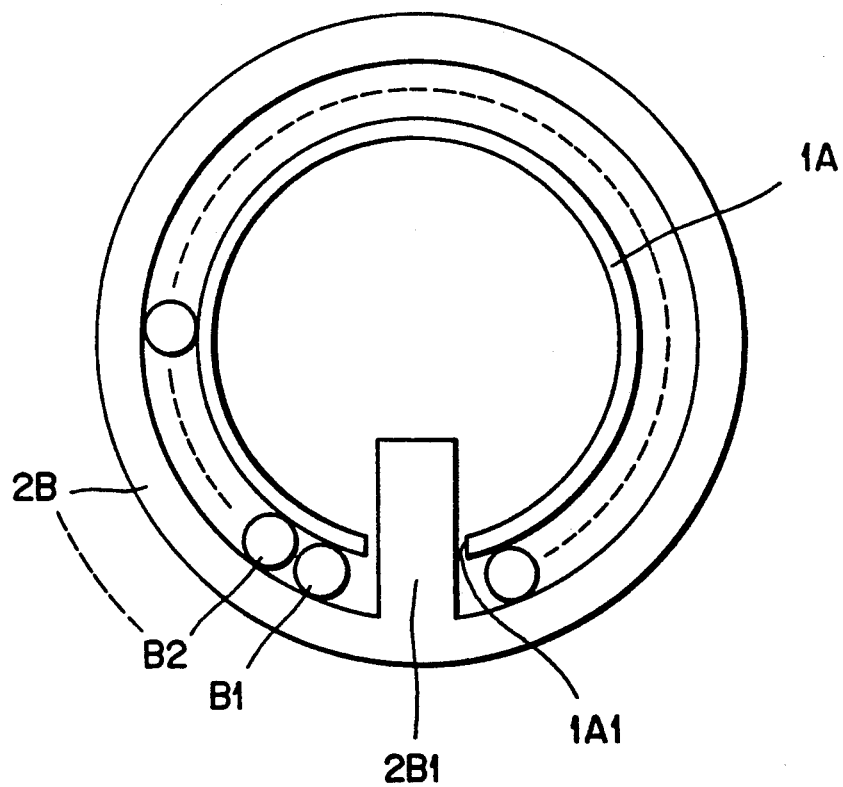
FIG. 5 is a drawing of the relationship between a receiver and a pole constituting the third embodiment of the present invention.

Moreover, a plurality of bearings B1, B2 . . . are arranged between the slider 2B and tube 1, whereby the slider 2B may slide more smoothly, as shown in FIG. 5.

The wire 9 elongates up inside of the tube 1, and elongates down as being suspended on a fixed pulley 10, thereafter the wire 9 goes out through an opening 1A4 at the bottom of the first tube 1A and is connected with the motor 5, as shown FIGS. 3 and 4.

The fixed pulley 10 is disposed on an inner wall 1A5 of the first tube 1A by means of mounting members 10A and 10B.

The motor 5 may be on the bottom plate 1A2 of the pole 1, and be connected with the sphygmomanometer 4 through a cord 6 as shown in FIG. 2, thereby the motor 5 is capable of being controlled from the sphygmomanometer 4.

That is to say, it is possible to carry out all the control of the motor 5 from the side of the sphygmomanometer 4, which control includes switching on the power supply, winding and unwinding the wire 9 etc.

The sphygmomanometer 4 may be a supersonic automatic sphygmomanometer, and put on the floor 11 through a table as shown in FIG. 2, or be put directly on the supporting plate 2A if it is.

The operation of the third embodiment will be explained hereinafter.

First, the bottom plate 1A2 of the pole 1 is put on the floor 11, and the disk 1B1 of the second tube 1B is made to push the ceiling 12 by adjusting the height of the tube while rotating the fastening member 8.

Thereby the pole 1 is fixed perpendicular to the floor 11.

Additionally, when the power supply of the motor 5 is switched on by operating the sphygmomanometer 4, the wire 9 is unwounded as shown in FIG. 3, whereby the receiver 2 is made to move down along the pole 1 and to stop at the position where the subject P will squat down.

In this state, the subject P is made to squat down, and after the cuff 3 connected with the sphygmomanometer 4 is wrapped around his arm, the arm with the cuff 3 is put on the receiver 2.

Thereafter, the body of the subject P remains in a stationary state during a fixed time, for example, 10 minutes.

Next, the subject P is made to stand up, and at the same time the wire 9 is wound with the motor 5, thereby the receiver 2 moves up as the body of the subject P moves up.

When the body of the subject P stops moving, the receiver 2 is also made to stop moving by switching off the power supply of the motor 5.

In this state, air is input into the cuff 3 through the tube 7, thereby blood pressure of the subject P is measured with the sphygmomanometer 4 based on the indirect method, as well known.

As described, according to the present invention, blood pressure of the subject can be measured, not in the rest state where he lie conventionally on the bed etc., but in the standing state.

Therefore, the present invention has the effect to discover easily the standing high blood pressure or standing low blood pressure.

I claim:

1. An apparatus for measuring blood pressure, comprising:
    a pole fixed perpendicular to a floor;
    a receiver module for supporting an arm of a patient;
    a cuff disposed on said module and adapted to be wound around the arm of said patient;
    a measuring device for measuring blood pressure;
    means for connecting said cuff with said measuring device for measuring blood pressure of said patient; and
    a coupling device mounting the module to the pole and slidable up and down along said pole as the body of said patient moves up and down, wherein after said patient remains stationary for a fixed time in a squatting position and stands up into a standing position, said measuring device measures the blood pressure of said patient.

2. The apparatus for measuring blood pressure as recited in claim 1, wherein said measuring device is a sphygmomanometer.

3. The apparatus for measuring blood pressure as recited in claim 1, further comprising means for comparing the blood pressure of said patient in said standing position with the blood pressure of said patient in said squatting position.

* * * * *